US009605020B2

(12) United States Patent
Matsuyama et al.

(10) Patent No.: US 9,605,020 B2
(45) Date of Patent: Mar. 28, 2017

(54) METHOD FOR PRODUCING DIPEPTIDE DERIVATIVE CONTAINING DISUBSTITUTED AMINO ACID RESIDUE

(71) Applicant: NAGASE & CO., LTD., Osaka (JP)

(72) Inventors: Keisuke Matsuyama, Hyogo (JP); Kazuya Kodama, Hyogo (JP)

(73) Assignee: NAGASE & CO., LTD., Osaka (JP)

( * ) Notice: Subject to any disclaimer, the term of this patent is extended or adjusted under 35 U.S.C. 154(b) by 0 days.

(21) Appl. No.: 14/914,458

(22) PCT Filed: Aug. 20, 2014

(86) PCT No.: PCT/JP2014/071804
§ 371 (c)(1),
(2) Date: Feb. 25, 2016

(87) PCT Pub. No.: WO2015/033781
PCT Pub. Date: Mar. 12, 2015

(65) Prior Publication Data
US 2016/0207958 A1    Jul. 21, 2016

(30) Foreign Application Priority Data
Sep. 3, 2013  (JP) ................. 2013-182231

(51) Int. Cl.
| | |
|---|---|
| C07C 229/00 | (2006.01) |
| C07K 5/065 | (2006.01) |
| C07B 51/00 | (2006.01) |
| C07K 5/062 | (2006.01) |
| C07K 5/072 | (2006.01) |

(52) U.S. Cl.
CPC .......... *C07K 5/06078* (2013.01); *C07B 51/00* (2013.01); *C07K 5/0606* (2013.01); *C07K 5/06026* (2013.01); *C07K 5/06034* (2013.01); *C07K 5/06043* (2013.01); *C07K 5/06095* (2013.01)

(58) Field of Classification Search
CPC ............ C07K 5/06078; C07K 5/06026; C07K 5/06034; C07K 5/06043; C07K 5/0606; C07K 5/06095; C07B 51/00
See application file for complete search history.

(56) References Cited

U.S. PATENT DOCUMENTS 4,818,749 A    4/1989    Gold et al.

FOREIGN PATENT DOCUMENTS

| JP | S59-31744 A | 2/1984 |
| JP | 1-163197 A | 6/1989 |
| NZ | 201001 A | 2/1986 |

OTHER PUBLICATIONS

Verarado et al. (a-N-Protected dipeptide acids: a simple and efficient synthesis via the easily accessible mixed anhydride method using free amino acids in DMSO and tetrabutylammonium hydroxide, J. Pept. Sci., 19, pp. 315-324, 2013.*
Verardo et al., "N-Protected dipeptide acids: a simple and efficient syntheses via the easily accessible mixed anhydride method using free amino acids in DMSO and tetrabutylammonium hydroxide", Journal of Peptide Science, 2013, pp. 315-324, vol. 19, No. 5.
Nebel et al., "Stereoselective synthesis of isovaline (IVA) and IVA-containing dipeptides for use in peptide synthesis", Tetrahedron, 1988, pp. 4793-4796, vol. 44, No. 15.
Tantry et al., "Synthesis of Na-protected peptide acids by N-C chain extension emptying O, N-bis-trimethylsilyl-amino acids using the mixed anhydride method", Indian Journal of Chemistry, Section B: Organic Chemistry Including Medicinal Chemistry, 2004, pp. 1282-1287, vol. 43B, No. 6.
Paira et al., "Peptide-Polymner Bioconjugates via Atom Transfer Radical Polymerization and Their Solution Aggregation into Hybrid Micro/Nanospheres for Dye Uptake", Macromolecules, 2010, pp. 4050-4061, vol. 43, No. 9.
International Search Report issued issued with respect to application No. PCT/JP2014/071804, mail date is Nov. 25, 2014.
International Preliminary Report issued issued with respect to application No. PCT/JP2014/071804, mail date is Mar. 8, 2016.

* cited by examiner

*Primary Examiner* — Yevegeny Valenrod
*Assistant Examiner* — Blaine G Doletski
(74) *Attorney, Agent, or Firm* — Greenblum & Bernstein, P.L.C.

(57) ABSTRACT

A method for producing a dipeptide that has a protected N-terminal and is represented by formula (1) or a salt of the dipeptide, said method comprising condensing an α-monosubstituted amino acid that has a protected N-terminal and is represented by formula (2) or glycine or a salt thereof with a disubstituted amino acid that is represented by formula (3) or a salt thereof in the presence of a condensing agent [in each of the formulae, substituents are as defined in the description or the like].

$$X-\underset{R^1}{\underset{|}{NR^2}}-\overset{O}{\underset{||}{C}}-\underset{H}{\underset{|}{N}}-\underset{Rb^2}{\overset{Ra^2}{\underset{|}{C}}}-CO_2H \quad (1)$$

$$X-\underset{NR^2}{\underset{|}{}}-\underset{R^1}{\overset{|}{CH}}-CO_2H \quad (2)$$

$$H_2N-\underset{Rb^2}{\overset{Ra^2}{\underset{|}{C}}}-CO_2H \quad (3)$$

4 Claims, No Drawings

METHOD FOR PRODUCING DIPEPTIDE DERIVATIVE CONTAINING DISUBSTITUTED AMINO ACID RESIDUE

TECHNICAL FIELD

The present invention relates to a method for producing a dipeptide derivative containing a disubstituted amino acid residue.

BACKGROUND ART

Peptides are compounds formed by the condensation of amino acids. The peptides exhibit various functions in vivo and are therefore expected to be applied as drugs. The peptide drugs are expected to exert various novel excellent functions by the examination of a novel amino acid sequence or the introduction of a non-natural amino acid, whereas the peptide drugs present problems such as rapid degradation by various enzymes in the body. In contrast to this, the introduction of disubstituted amino acids with their α-carbon atoms each substituted by two substituents to peptides has been found to be able to enhance the stability of the peptides against peptidases in vivo.

CITATION LIST

Patent Literature

Patent Literature 1: Japanese Patent Laid-Open No. 1-163197
Patent Literature 2: Japanese Patent Laid-Open No. 59-31744

SUMMARY OF INVENTION

Technical Problem

In peptide synthesis, a general solid-phase peptide synthesis method involves binding an amino acid having a protected amino group through its carboxyl group to a resin for solid-phase synthesis, then deprotecting the amino group, binding thereto a next amino acid having a protected amino group, and repeating this deprotection and binding to obtain peptides. The obtained peptides are finally excised from the resin.

In the case of producing peptides having a disubstituted amino acid residue by the solid-phase peptide synthesis method, the binding of the next amino acid residue to the N-terminus of the disubstituted amino acid residue may result in low reactivity due to steric hindrance around asymmetric carbon of the disubstituted amino acid residue.

For this reason, the solid-phase synthesis is continued while the amino acid residue to follow the disubstituted amino acid residue is partially defective. The resulting peptides excised from the resin for solid-phase synthesis include by-products containing which partially lack the amino acid residue to follow the disubstituted amino acid residue. The synthesis of the peptides containing a disubstituted amino acid residue disadvantageously ends in low yields or purity.

Accordingly, a dipeptide derivative in which an amino acid having a protected amino group is bound with the amino group of the disubstituted amino acid is synthesized in advance. Utilization of this dipeptide derivative in solid-phase peptide synthesis can be expected to circumvent the low reactive process as described above.

The conventional dipeptide derivative having a protected N-terminal amino group is typically synthesized by a method which involves condensing an amino acid having a protected amino group with an amino acid having an ester-protected carboxyl group in the presence of a condensing agent, followed by the deesterification of the protecting ester group in the carboxyl group, in order to avoid forming random peptide bonds (see e.g., Patent Literatures 1 and 2).

The synthesis method described above is reliable, but requires a large number of steps. In addition, when each constituent amino acid has a protecting group at its side chain, the deesterification of the protecting ester group might be difficult depending on the type of the protecting group.

The present invention has been made in light of these circumstances. An object of the present invention is to provide a method for producing a dipeptide derivative, which requires a fewer number of steps than that of the conventional method for producing a dipeptide and is capable of producing the desired dipeptide derivative at high yields, regardless of the type of a protecting group in the side chain of each constituent amino acid.

Solution to Problem

The present inventors have conducted diligent studies and consequently completed the present invention by finding that, surprisingly, the dipeptide derivative of interest can be obtained in one step at high yields without causing random peptide bond reaction of concern, provided that an unprotected amino acid whose carboxyl group is not ester-protected, if used as a starting material, is a disubstituted amino acid.

Specifically, the present invention provides a method for producing an N-terminal protected dipeptide represented by the following formula (1) or a salt thereof:

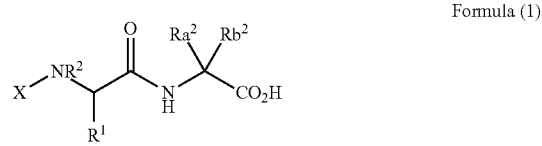

Formula (1)

wherein X represents a protecting group for an amino group, $R^1$ represents a side chain of an α-monosubstituted amino acid, or a hydrogen atom, wherein the side chain is optionally protected,
$R^2$ represents a group bonded to $R^1$ to form the side chain, or a hydrogen atom, and
$Ra^2$ and $Rb^2$ each independently represent an alkyl group optionally having a substituent, an alkenyl group optionally having a substituent, an alkynyl group optionally having a substituent, or an aralkyl group optionally having a substituent,
the production method comprising condensing
an N-terminal protected α-monosubstituted amino acid or glycine represented by the following formula (2), or a salt of the amino acid or glycine:

Formula (2)

wherein X, $R^1$, and $R^2$ are as defined for X, $R^1$, and $R^2$, respectively, in the formula (1), with a disubstituted amino acid represented by the following formula (3) or a salt thereof:

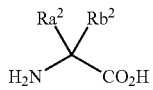

Formula (3)

wherein $Ra^2$ and $Rb^2$ are as defined for $Ra^2$ and $Rb^2$, respectively, in the formula (1)
in the presence of a condensing agent.

The adopted method for producing a dipeptide derivative according to the present invention requires a fewer number of steps than that of the conventional method for producing a dipeptide and is capable of producing the desired dipeptide derivative at high yields, regardless of the type of a protecting group in the side chain of each constituent amino acid.

In the production method, preferably, the N-terminal protected α-monosubstituted amino acid or glycine represented by the formula (2), or a salt of the amino acid or glycine is condensed with the disubstituted amino acid represented by the formula (3) or a salt thereof in the presence of a stoichiometric amount or more of the condensing agent. The presence of a stoichiometric amount or more of the condensing agent allows the condensation reaction to proceed more efficiently.

In the production method, preferably, the reaction of the N-terminal protected α-monosubstituted amino acid or glycine represented by the formula (2), or a salt of the amino acid or glycine with the disubstituted amino acid or a salt thereof is terminated when the rate of reaction of the N-terminal protected α-monosubstituted amino acid or glycine represented by the formula (2), or a salt of the amino acid or glycine reaches 70 to 80%. This can prevent a further amino acid from being condensed with the carboxyl group of the dipeptide derivative of interest and can therefore produce the desired dipeptide derivative at higher yields.

Advantageous Effects of Invention

The present invention can provide a method for producing a dipeptide derivative, which requires a fewer number of steps than that of the conventional method for producing a dipeptide and is capable of producing the desired dipeptide derivative at high yields, regardless of the type of a protecting group in the side chain of each constituent amino acid.

DESCRIPTION OF EMBODIMENTS

Hereinafter, preferred embodiments of the present invention will be described. However, the present invention is not intended to be limited by these embodiments by any means.

In the present specification, each amino acid is also indicated by its three-letter code or one-letter code. Specifically, for example, each amino acid may be indicated as follows: Ala or A for alanine, Arg or R for arginine, Asn or N for asparagine, Asp or D for aspartic acid, Cys or C for cysteine, Glu or E for glutamic acid, Gln or Q for glutamine, Gly or G for glycine, His or H for histidine, Ile or I for isoleucine, Leu or L for leucine, Lys or K for lysine, Met or M for methionine, Phe or F for phenylalanine, Pro or P for proline, Ser or S for serine, Thr or T for threonine, Trp or W for tryptophan, Tyr or Y for tyrosine, and Val or V for valine.

In the present embodiment, the method for producing an N-terminal protected dipeptide represented by the following formula (1) or a salt thereof:

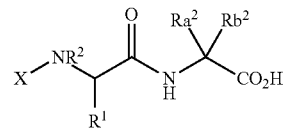

Formula (1)

wherein X represents a protecting group for an amino group, $R^1$ represents a side chain of an α-monosubstituted amino acid, or a hydrogen atom, wherein the side chain is optionally protected,
$R^2$ represents a group bonded to $R^1$ to form the side chain, or a hydrogen atom, and
$Ra^2$ and $Rb^2$ each independently represent an alkyl group optionally having a substituent, an alkenyl group optionally having a substituent, an alkynyl group optionally having a substituent, or an aralkyl group optionally having a substituent, comprises condensing
an N-terminal protected α-monosubstituted amino acid or glycine represented by the following formula (2), or a salt of the amino acid or glycine:

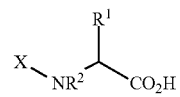

Formula (2)

wherein X, $R^1$, and $R^2$ are as defined for X, $R^1$, and $R^2$, respectively, in the formula (1),
with a disubstituted amino acid represented by the following formula (3) or a salt thereof:

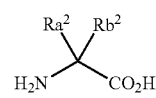

Formula (3)

wherein $Ra^2$ and $Rb^2$ are as defined for $Ra^2$ and $Rb^2$, respectively, in the formula (1)
in the presence of a condensing agent.

In this context, the condensing agent usually refers to a chemical reagent for chemical synthesis and offers a condensation product by eliminating one molecule of water from a substrate. Those skilled in the art understand that the condensing agent differs from biocatalysts, such as enzymes, for use in fermentation methods, etc. The biocatalysts have high substrate specificity, and a biocatalyst suitable for each peptide of interest must be used. In addition, it is usually difficult to find an appropriate biocatalyst, particularly when a non-natural amino acid such as a disubstituted amino acid is used as the substrate.

The condensing agent used in the present embodiment can be used without particular limitations as long as the condensing agent is generally used in chemical synthesis reaction and generally known to those skilled in the art. The condensing agent may be, for example, at least one selected from the group consisting of HBTU (2-(1H-benzotriazol-1- yl)-1,1,3,3-tetramethyluronium hexafluorophosphate), DCC (dicyclohexylcarbodiimide), and EDC (1-ethyl-3-(3-dimethylaminopropyl)carbodiimide). Among them, HBTU is particularly preferred.

In the present embodiment, a stoichiometric amount or more of the condensing agent is preferably present in the reaction system. Specifically, in the present embodiment, the condensing agent is preferably present at equimolar amount or more compared to water generated by the dehydration condensation reaction of the N-terminal protected α-monosubstituted amino acid or glycine represented by the formula (2), or a salt of the amino acid or glycine with the disubstituted amino acid represented by the formula (3) or a salt thereof. This allows the condensation reaction to proceed more efficiently.

In the N-terminal protected α-monosubstituted amino acid or glycine represented by the formula (2), or a salt of the amino acid or glycine as the starting material according to the present embodiment, X represents a protecting group for an amino group. Any protecting group for an amino group generally known to those skilled in the art can be adopted as the protecting group for an amino group without particular limitations. The protecting group for an amino group may be, for example, at least one selected from the group consisting of carbamates such as Fmoc (9-fluorenylmethoxycarbonyl), Z (benzyloxycarbonyl), Alloc (allyloxycarbonyl), Troc (2,2,2-trichloroethoxycarbonyl), and Boc (t-butyloxycarbonyl), and amides such as Ac (acetyl) and Bz (benzoyl). Among them, Fmoc is particularly preferred.

In the N-terminal protected α-monosubstituted amino acid or glycine represented by the formula (2), or a salt of the amino acid or glycine, $R^1$ represents an optionally protected side chain of an α-monosubstituted amino acid, or a hydrogen atom. Any of natural and non-natural α-monosubstituted amino acids can be adopted. Also, any of D- and L-forms can be used. Preferred examples of the side chain of such an α-monosubstituted amino acid include a side chain Me of Ala, a side chain $-CH_2CH_2CH_2NHC(=NH)NH_2$ of Arg, a side chain $-CH_2CONH_2$ of Asn, a side chain $-CH_2COOH$ of Asp, a side chain $-CH_2SH$ of Cys, a side chain $-CH_2CH_2COOH$ of Glu, a side chain $-CH_2CH_2CONH_2$ of Gln, a side chain $-CH_2Im$ (wherein Im represents a 4-imidazolyl group) of His, a side chain $-CH(CH_3)CH_2CH_3$ of Ile, a side chain $-CH_2CH(CH_3)_2$ of Leu, a side chain $-CH_2CH_2CH_2CH_2NH_2$ of Lys, a side chain $-CH_2CH_2SCH_3$ of Met, a side chain $-CH_2Ph$ of Phe, a side chain $-CH_2OH$ of Ser, a side chain $-CH(OH)CH_3$ of Thr, a side chain $-CH_2Ind$ (wherein Ind represents a 3-indolyl group) of Trp, a side chain $-CH_2(4-OH-Ph)$ of Tyr, a side chain $-CH(CH_3)_2$ of Val, a side chain $-CH_2CH_2SH$ of homocysteine, and a side chain $-CH_2CH=CH_2$ of allylglycine. Among them, a side chain $-CH(OH)CH_3$ of Thr, a side chain $-CH_2CH_2CH_2NHC(=NH)NH_2$ of Arg, a side chain $-CH_2CH(CH_3)_2$ of Leu, a side chain $-CH_2Ph$ of Phe, a side chain $-CH_2CH_2SH$ of homocysteine, or a side chain $-CH_2CH=CH_2$ of allylglycine is more preferred.

The side chain of the α-monosubstituted amino acid may be protected. The protecting group that protects the side chain is not particularly limited and can be appropriately selected from those used as general protecting groups for a side chain. The protecting group can be, for example, at least one selected from the group consisting of Pbf (2,2,4,6,7-pentamethyl-2,2-dihydrobenzofuran-5-sulfonyl) that is a protecting group for a guanidyl group, t-butyl that is a protecting group for a hydroxy group, trityl that is a protecting group for a thiol group, Fmoc, Z, Troc, Ac, Bz, and Boc that are protecting groups for an amino group, and benzyl that is a protecting group for an indolyl group.

In the N-terminal protected α-monosubstituted amino acid or glycine represented by the formula (2), or a salt of the amino acid or glycine, $R^2$ represents a group bonded to $R^1$ to form the side chain, or a hydrogen atom. When $R^2$ is bonded to $R^1$ to form the side chain, $R^1$ and $R^2$ form a cyclic group together with the carbon atom adjacent to $R^1$ and the nitrogen atom adjacent to $R^2$. Such a cyclic group is not particularly limited as long as the cyclic group has a nitrogen-containing cyclic structure. For example, a 5- to 15-membered monocyclic, bicyclic, or tricyclic ring can be formed. This ring may be a saturated ring or may be a partially unsaturated ring. The ring optionally has a substituent. Examples of the cyclic group as described above can include pyrrolidine and piperidine.

The N-terminal protected α-monosubstituted amino acid or glycine represented by the formula (2) can also be used as a salt in some cases. Examples of the salt of the N-terminal protected α-monosubstituted amino acid or glycine include sodium salt, potassium salt, lithium salt, calcium salt, magnesium salt, and dicyclohexylamine (DCHA) salt.

Preferred examples of the N-terminal protected α-monosubstituted amino acid or glycine represented by the formula (2), or a salt of the amino acid or glycine as such a starting material according to the present embodiment are shown below.

Fmoc-Gly-OH
Fmoc-Thr(Ot-Bu)-OH
Fmoc-D-Phe-OH
Fmoc-D-Hcy(Tr)-OH
Fmoc-Hcy(Tr)-OH
Fmoc-Arg (Pbf)-OH
Fmoc-Leu-OH
Fmoc-Phe-OH
Ac-(allyl)Gly-OH
Boc-(allyl)Gly-OH*DCHA In the disubstituted amino acid represented by the formula (3) or a salt thereof as the starting material according to the present embodiment, $Ra^2$ and $Rb^2$ each independently represent an alkyl group optionally having a substituent, an alkenyl group optionally having a substituent, or an alkynyl group optionally having a substituent. The alkyl group, the alkenyl group, and the alkynyl group can each have, for example, a linear or branched structure having 1 to 14 (preferably, 1 to 8) carbon atoms. Preferred examples of the substituent include, but are not limited to, halo, nitro, optionally protected hydroxy, optionally protected mercapto, optionally halo-substituted alkoxy, optionally substituted aryl (e.g., phenyl), carboxy or ester thereof, optionally substituted or protected amino, and optionally substituted or protected heteroaryl (e.g., indole).

One of $Ra^2$ and $Rb^2$ is more preferably methyl. The substitution of a monosubstituted amino acid by a peptide containing the disubstituted amino acid wherein one of $Ra^2$ and $Rb^2$ is methyl often facilitates producing, particularly, effects such as improvement in stability while maintaining, for example, the effect of the peptide as a drug.

The disubstituted amino acid represented by the formula (3) can also be used as a salt. Examples of the salt of the disubstituted amino acid include sodium salt, potassium salt, lithium salt, calcium salt, magnesium salt, dicyclohexylamine (DCHA) salt, hydrochloride, sulfate, nitrate, perchlorate, and hydrobromide.

Preferred examples of the disubstituted amino acid represented by the formula (3) as the starting material according to the present embodiment are shown below.

(S)-α-(4-pentenyl)Ala-OH
(R)-α-(4-pentenyl)Ala-OH
(S)-α-(7-octenyl)Ala-OH
(R)-α-(7-octenyl)Ala-OH
(S)-α-(allyl)Ala-OH.$H_2O$
(R)-α-(allyl)Ala-OH.$H_2O$
(S)-α-(propargyl)Ala-OH
(R)-α-(propargyl)Ala-OH
(S)-α-(ethyl)Ala-OH.$H_2O$
(R)-α-(ethyl)Ala-OH.$H_2O$
(S)-α-Me-Asp(Ot-Bu)-OH
(R)-α-Me-Asp (Ot-Bu)-OH
(S)-α-Me-Leu-OH
(R)-α-Me-Leu-OH
(S)-α-Me-Phe-OH.$H_2O$
(R)-α-Me-Phe-OH.$H_2O$
(S)-α-Me-Val-OH
(R)-α-Me-Val-OH
(S)-α-Me-o-fluoroPhe-OH
(R)-α-Me-o-fluoroPhe-OH
(S)-α-Me-m-fluoroPhe-OH
(R)-α-Me-m-fluoroPhe-OH
(S)-α-Me-p-fluoroPhe-OH
(R)-α-Me-p-fluoroPhe-OH
(S)-α-Me-2,6-difluoroPhe-OH
(R)-α-Me-2,6-difluoroPhe-OH
(S)-α-Me-p-$CF_3$O-Phe-OH
(R)-α-Me-p-$CF_3$O-Phe-OH
(S)-α-Me-o-bromoPhe-OH.$H_2O$
(R)-α-Me-o-bromoPhe-OH.$H_2O$
(S)-α-Me-m-bromoPhe-OH—$H_2O$
(R)-α-Me-m-bromoPhe-OH.$H_2O$
(S)-α-Me-p-bromoPhe-OH
(R)-α-Me-p-bromoPhe-OH
(S)-α-Me-m-iodoPhe-OH.$H_2O$
(R)-α-Me-m-iodoPhe-OH.$H_2O$
(S)-α-Me-p-iodoPhe-OH
(R)-α-Me-p-iodoPhe-OH
(S)-α-Me-o-nitroPhe-OH.$H_2O$
(R)-α-Me-o-nitroPhe-OH.$H_2O$
(S)-α-Me-m-nitroPhe-OH.$H_2O$
(R)-α-Me-m-nitroPhe-OH.$H_2O$
(S)-α-Me-p-phenyl Phe-OH.$H_2O$ In the present embodiment, the ratio between the N-terminal protected α-monosubstituted amino acid or glycine represented by the formula (2), or a salt of the amino acid or glycine and the disubstituted amino acid represented by the formula (3) or a salt thereof as the starting materials, when they are charged, is not particularly limited and can be appropriately changed empirically by those skilled in the art in consideration of, for example, the physical properties of each starting material used and easy removal for the possible removal of an excess after the completion of the condensation reaction. In the case of using, for example, a theoretical equivalent or more of the disubstituted amino acid represented by the formula (3) to the N-terminal protected α-monosubstituted amino acid or glycine represented by the formula (2), those skilled in the art can use a general approach to remove an excess of the disubstituted amino acid represented by the formula (3) after the completion of the reaction.

In the production method according to the present embodiment, the time of the condensation of the N-terminal protected α-monosubstituted amino acid or glycine represented by the formula (2) and the disubstituted amino acid represented by the formula (3) as the starting materials is preferably controlled while the respective amounts of the compounds of the formulas (1), (2), and (3) that change with the progression of the condensation reaction are monitored.

The time for the condensation reaction differs depending on the types of the starting materials used, various reaction conditions, etc. A short condensation time results in low yields due to the insufficient formation of the dipeptide represented by the formula (1). A long condensation time results in low yields of the desired dipeptide represented by the formula (1) due to the further reaction of the carboxyl group in the dipeptide represented by the formula (1). From such viewpoints, in the present embodiment, the reaction is preferably terminated when the rate of reaction of the N-terminal protected α-monosubstituted amino acid or glycine represented by the formula (2), or a salt of the amino acid or glycine reaches 70 to 80%. In this context, the rate of reaction is indicated by the ratio of the consumption of the starting material with the progression of the reaction to the amount of the starting material charged. The monitoring described above can be carried out by the adoption of any of various monitoring methods generally known to those skilled in the art. Preferred examples thereof include a method which involves sampling the reaction mixture in the course of the reaction and analyzing the sample by HPLC. In this case, for example, the total peak area $S_0$ of the starting material N-terminal protected α-monosubstituted amino acid or glycine, a dipeptide, a tripeptide, a tetrapeptide, and a pentapeptide in a chromatogram obtained by HPLC analysis is regarded as the amount of the N-terminal protected α-monosubstituted amino acid or glycine charged. The rate of reaction can be calculated from the total peak area $S_0$ and the peak area $S_1$ of the N-terminal protected α-monosubstituted amino acid or glycine according to the expression: Rate of reaction (%)=$(1-S_1/S_0)\times 100$.

In the production method according to the present embodiment, the solvent for use in the condensation reaction is not particularly limited and can be appropriately selected from solvents known in the art generally used in condensation reaction for peptide synthesis. Preferred examples of such a solvent include THF, DMF, and NMP.

In the production method according to the present embodiment, the temperature for the condensation reaction is not particularly limited and can be appropriately set within a temperature range that may be generally used by those skilled in the art for peptide synthesis. The reaction is preferably carried out at room temperature because of easy operation.

The N-terminal protected dipeptide represented by the formula (1) produced by the production method according to the present embodiment can be obtained in a highly pure state. In order to further enhance the purity of the obtained N-terminal protected dipeptide represented by the formula (1), the N-terminal protected dipeptide may be isolated and purified with high purity by use of any of various approaches generally known to those skilled in the art.

In the N-terminal protected dipeptide represented by the formula (1) according to the present embodiment that can be thus produced, X, $R^1$, $R^2$, $Ra^2$, and $Rb^2$ are as defined for their respective substituents in the formula (2) or the formula (3).

The N-terminal protected dipeptide represented by the formula (1) can also be obtained as a salt in some cases.

The method for producing the N-terminal protected dipeptide represented by the formula (1) according to the present embodiment can omit a carboxyl group deprotection step and can therefore decrease the number of production steps, as compared with the conventional method for producing a dipeptide. In addition, the N-terminal protected dipeptide represented by the formula (1) of interest can be obtained at high yields without causing random peptide bond formation of concern, provided that a disubstituted amino acid is used as a starting material even if the carboxyl group is not ester protected.

The dipeptide represented by the formula (1) produced by the method according to the present embodiment has a protected N-terminal amino group. Thus, the dipeptide is suitable for use as a starting material dipeptide in a solid-phase peptide synthesis method.

In the case of synthesizing peptides containing a disubstituted amino acid residue by a generally adopted approach, i.e., an approach of binding amino acids one by one, in the solid-phase peptide synthesis method, the influence of steric hindrance around asymmetric carbon of the disubstituted amino acid residue might reduce the reactivity of its N-terminus and cause reduction in yields. By contrast, use of the N-terminal protected dipeptide represented by the formula (1) in the solid-phase peptide synthesis method can suppress the influence of such steric hindrance and can enhance the reactivity for newly binding the next amino acid to the N-terminus of the bound dipeptide. This prevents the formation of by-product amino acid-defective forms. As a result, the peptides containing a disubstituted amino acid residue can be synthesized with higher efficiency and purity.

A method for synthesizing a peptide using the N-terminal protected dipeptide represented by the formula (1) obtained by the production method according to the present embodiment can employ a solid-phase peptide synthesis method generally known to those skilled in the art. Preferred examples of the resin support for solid-phase synthesis used can include, but are not limited to, Rink Amide MBHA resin (100 to 200 mesh).

EXAMPLES

Hereinafter, the present invention will be described in more detail by reference to Examples. However, the present invention is not intended to be limited by these examples.

In the description below, the following abbreviations are used:
Fmoc: 9-fluorenylmethoxycarbonyl;
THF: tetrahydrofuran;
HBTU: 2-(1H-benzotriazol-1-yl)-1,1,3,3-tetramethyluronium hexafluorophosphate;
TEA: triethylamine;
MTBE: methyl t-butyl ether;
Hcy: homocysteine;
Tr: trityl;
NMP: N-methylpiperidone;
HOBt: 1-hydroxybenzotriazole;
DIPEA: diisopropylethylamine;
TFA: trifluoroacetic acid; and
Pbf: 2,2,4,6,7-pentamethyl-2,2-dimethylbenzofuran-5-sulfonyl.

Production of N-Terminal Protected Dipeptide Represented by Formula (1)

Example 1

Synthesis of Fmoc-Gly-(R)-α-(4-pentenyl)Ala-OH

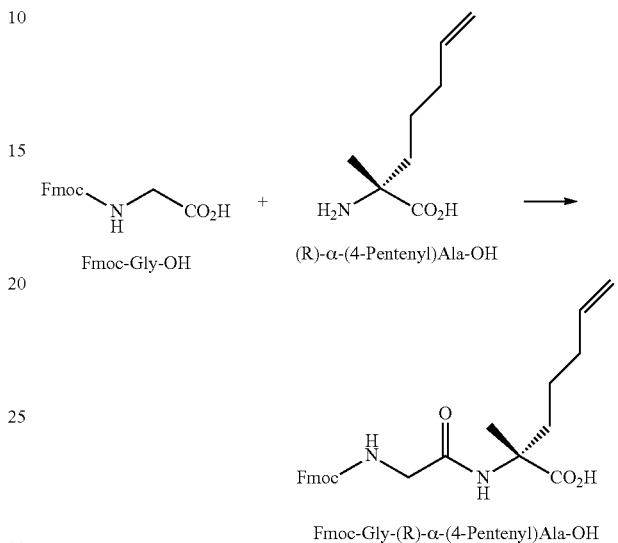

Fmoc-Gly-(R)-α-(4-Pentenyl)Ala-OH

A 25 mL reaction vessel was charged with 0.64 g (2.2 mmol) of Fmoc-Gly-OH and 0.38 g (2.4 mmol) of (R)-α-(4-pentenyl)Ala-OH, which were then suspended in THF (7.7 mL). To this suspension, 1.19 g (3.14 mmol) of HBTU and 0.49 mL (3.5 mmol) of TEA were added, and the mixture was stirred at room temperature for 23 hours.

The reaction mixture was sampled in the course of the reaction and analyzed by HPLC (detection: 264 nm, UV). The area ratio of the respective peaks corresponding to
Fmoc-Gly-OH,
Fmoc-Gly-(R)-α-(4-pentenyl)Ala-OH (dipeptide),
Fmoc-Gly-(R)-α-(4-pentenyl)Ala-(R)-α-(4-pentenyl) Ala-OH (tripeptide),
Fmoc-Gly-(R)-α-(4-pentenyl)Ala-(R)-α-(4-pentenyl) Ala-(R)-α-(4-pentenyl)Ala-OH (tetrapeptide), and
Fmoc-Gly-(R)-α-(4-pentenyl)Ala-(R)-α-(4-pentenyl) Ala-(R)-α-(4-pentenyl)Ala-(R)-α-(4-pentenyl)Ala-OH (pentapeptide)
was 31:68:1.5:0.065:undetected (rate of reaction: 69%) in 4.5 hours, 30:68:2.0:0.091:undetected (rate of reaction: 70%) in 5.5 hours, 27:70:3.2:0.17:undetected (rate of reaction: 73%) in 7.9 hours, and 24:68:7.6:0.45:0.047 (rate of reaction: 76%) in 23 hours. The rate of reaction was calculated from the ratio of the area of Fmoc-Gly-OH to the total area of Fmoc-Gly-OH, the dipeptide, the tripeptide, the tetrapeptide, and the pentapeptide.

Tap water (8 mL) and ethyl acetate (8 mL) were added to the reaction mixture, and the mixture was stirred at room temperature and then left standing to separate between organic and aqueous layers. The organic layer was washed with a saturated aqueous solution of sodium bicarbonate (40 mL), tap water (8 mL), and 0.5 mol/L hydrochloric acid (12 mL) successively and then concentrated in vacuo. To the residue, MTBE (11 mL), normal-hexane (1 mL), and ethyl acetate (9 mL) were added, the residue was dispersed, and the mixture was left standing, followed by the removal of the supernatant. To the residue, MTBE (6 mL) was added, the residue was dispersed, and the mixture was left standing, followed by the removal of the supernatant. The residue was dried to give 0.23 g of Fmoc-Gly-(R)-α-(4-pentenyl)Ala-OH as off-white crystals (yield: 24%).

Fmoc-Gly-(R)-α-(4-pentenyl)Ala-OH;
Melting point: 130 to 133° C. (uncorrected).
$^{1}$HNMR (400 MHz, CDCl$_3$) δ ppm: 1.2-1.4 (m, 2H); 1.60 (s, 3H); 1.86 (dt, J$_1$=12.8 Hz, J$_2$=4.7 Hz, 1H); 1.9-2.1 (m, 2H); 2.16 (dt, J$_1$=12.8 Hz, J$_2$=3.6 Hz, 1H); 3.8-4.0 (m, 2H); 4.21 (t, J=7.2 Hz, 1H); 4.39 (d, J=7.2 Hz, 2H); 4.9-5.0 (m, 2H); 5.70 (dt, J$_1$=12.0 Hz, J$_2$=10.0 Hz, 1H); 5.78 (br.s, 1H); 6.87 (br.s, 1H); 7.30 (dt, J$_1$=7.5 Hz, J$_2$=0.9 Hz, 2H); 7.39 (t, J=7.5 Hz, 2H); 7.58 (d, J=7.5 Hz, 2H); 7.75 (d, J=7.5 Hz, 2H).
HRMS m/z: 437.2071 (calcd for C$_{25}$H$_{29}$N$_2$O$_5$ ([M+H]$^+$)); 437.2078 (found).

Fmoc-Gly-(R)-α-(4-pentenyl)Ala-(R)-α-(4-pentenyl)Ala-OH;
HRMS m/z: 576.3068 (calcd for C$_{33}$H$_{42}$N$_3$O$_6$ ([M+H]+)); 576.3072 (found).

Fmoc-Gly-(R)-α-(4-pentenyl)Ala-(R)-α-(4-pentenyl)Ala-(R)-α-(4-pentenyl)Ala-OH;
HRMS m/z: 715.4065 (calcd for C$_{41}$H$_{55}$N$_4$O$_7$ ([M+H]$^+$)); 715.4063 (found).

Fmoc-Gly-(R)-α-(4-pentenyl)Ala-(R)-α-(4-pentenyl)Ala-(R)-α-(4-pentenyl)Ala-(R)-α-(4-pentenyl)Ala-OH;
HRMS m/z: 854.5062 (calcd for C$_{49}$H$_{67}$N$_5$O$_8$ ([M+H]$^+$)); 854.5061 (found).

Example 2

Synthesis of Fmoc-Thr (Ot-Bu)-(S)-α-Me-o-fluoroPhe-OH

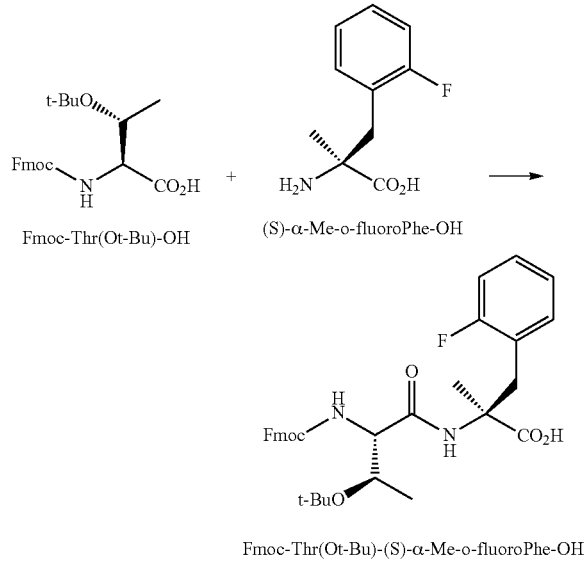

A 100 mL reaction vessel was charged with 2.17 g (5.46 mmol) of Fmoc-Thr(Ot-Bu)-OH and 1.45 g (7.35 mmol) of (S)-α-Me-o-fluoroPhe-OH, which were then suspended in THF (28 mL). To this suspension, 6.80 g (17.9 mmol) of HBTU and 2.56 mL (1.84 mmol) of TEA were added, and the mixture was stirred at room temperature for 62 hours. Tap water (35 mL) and ethyl acetate (48 mL) were added to the reaction mixture, and the mixture was stirred at room temperature and then left standing to separate between organic and aqueous layers. To the organic layer, 0.5 mol/L hydrochloric acid (34 mL) was added, and the mixture was stirred at room temperature for 3.5 hours and then left standing to separate between organic and aqueous layers. To the organic layer, a saturated aqueous solution of sodium bicarbonate (56 mL) was added, and the mixture was stirred, then suction-filtered, and thoroughly washed with ethyl acetate (6 mL). The filtrate and the washes were left standing to separate between organic and aqueous layers. The organic layer was washed with a saturated aqueous solution of sodium bicarbonate (14 mL), 0.5 mol/L hydrochloric acid (6 mL), and tap water (42 mL) successively and then concentrated in vacuo. The residue was purified by silica gel column chromatography to give 0.35 g of Fmoc-Thr(Ot-Bu)-(S)-α-Me-o-fluoroPhe-OH as a white amorphous solid (yield: 11%).

Melting point: 61 to 81° C. (uncorrected).
HRMS m/z: 577.2078 (calcd for C$_{33}$H$_{37}$FN$_2$O$_6$ ([M+H]$^+$)); 577.2710 (found).

Example 3

Synthesis of Fmoc-Thr(Ot-Bu)-(S)-α-Me-o-fluoroPhe-OH

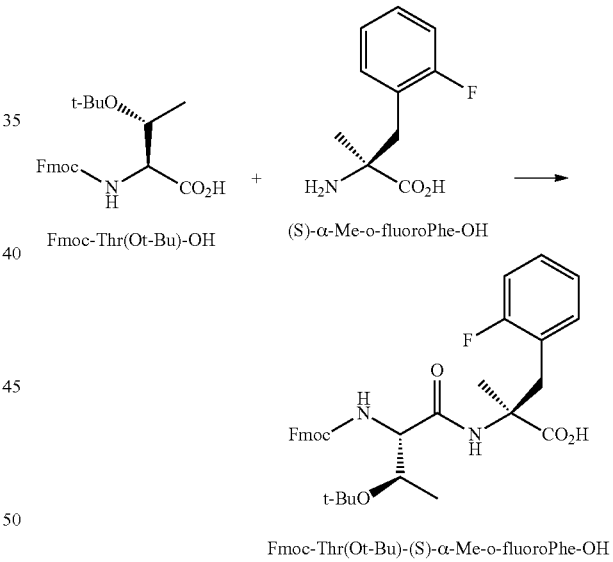

A 50 mL reaction vessel was charged with 1.17 g (2.94 mmol) of Fmoc-Thr(Ot-Bu)-OH and 0.73 g (3.7 mmol) of (S)-α-Me-o-fluoroPhe-OH, which were then suspended in THF (14 mL). To this suspension, 3.41 g (8.99 mmol) of HBTU and 1.26 mL (9.04 mmol) of TEA were added, and the mixture was stirred at room temperature for 31 hours.

The reaction mixture was sampled in the course of the reaction and analyzed by HPLC (detection: 264 nm, UV).

The area ratio of the respective peaks corresponding to
Fmoc-Thr(Ot-Bu)-OH,
Fmoc-Thr(Ot-Bu)-α-Me-o-fluoroPhe-OH (dipeptide), and
Fmoc-Thr(Ot-Bu)-α-Me-o-fluoroPhe-α-Me-o-fluoroPhe-OH (tripeptide)

was 23:76:1.7 (rate of reaction: 77%) in 22 hours, and 20:78:1.9 (rate of reaction: 80%) in 31 hours. The rate of reaction was calculated from the ratio of the area of Fmoc-Thr(Ot-Bu)-OH to the total area of Fmoc-Thr(Ot-Bu)-OH, the dipeptide, the tripeptide, the tetrapeptide, and the pentapeptide. However, the peaks of the tetrapeptide and the pentapeptide were undetected.

The ratio between two main isomers of Fmoc-Thr(Ot-Bu)-α-Me-o-fluoroPhe-OH was 97.3:2.7 in 22 hours and 97.4:2.6 in 31 hours.

Fmoc-Thr(Ot-Bu)-α-Me-o-fluoroPhe-OH;

HRMS m/z: 756.3455 (calcd for $C_{43}H_{48}F_2N_3O_7$ ([M+H]$^+$)); 756.3455 (found).

Example 4

Synthesis of Fmoc-D-Hcy(Tr)-(S)-α-Me-o-fluoroPhe-OH

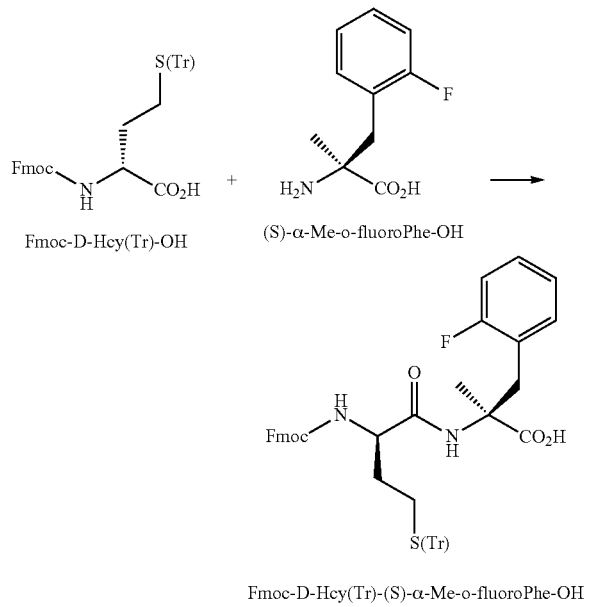

Fmoc-D-Hcy(Tr)-(S)-α-Me-o-fluoroPhe-OH

A 25 mL reaction vessel was charged with 0.28 g (0.45 mmol) of Fmoc-D-Hcy(Tr)-OH and 0.11 g (0.56 mmol) of (S)-α-Me-o-fluoroPhe-OH, which were then suspended in THF (2 mL). To this suspension, 0.52 g (1.4 mmol) of HBTU and 0.20 mL (1.4 mmol) of TEA were added, and the mixture was stirred at room temperature for 5.8 hours. Tap water (2.5 mL) and ethyl acetate (3.5 mL) were added to the reaction mixture, and the mixture was stirred at room temperature and then left standing to separate between organic and aqueous layers. The organic layer was washed with a saturated aqueous solution of sodium bicarbonate (4 mL), 0.5 mol/L hydrochloric acid (2 mL), and tap water (6 mL) successively and then concentrated in vacuo. To the residue, ethyl acetate (1.9 mL) was added, and the residue was dispersed, and the mixture was left standing, and then suction-filtered. The resulting white powder was dried to give 0.21 g of Fmoc-D-Hcy(Tr)-(S)-α-Me-o-fluoroPhe-OH (yield: 59%).

$^1$HNMR (400 MHz, CDCl$_3$) δ ppm: 1.3-1.6 (m, 1H); 1.46 (s, 3H); 1.6-1.8 (m, 1H); 2.1-2.3 (m, 2H); 3.23 (d, J=14.0 Hz, 1H); 3.32 (d, J=14.0 Hz, 1H); 4.0-4.2 (m, 2H); 4.17 (t, J=6.6 Hz, 1H); 4.34 (d, J=6.6 Hz, 2H); 5.29 (d, J=8.0 Hz, 1H); 6.49 (s, 1H); 6.9-7.0 (m, 2H); 7.07 (t, J=7.0 Hz, 1H); 7.1-7.5 (m, 20H); 7.57 (d, J=7.0 Hz, 2H); 7.74 (d, J=7.0 Hz, 2H)

Example 5

Synthesis of Fmoc-Hcy(Tr)-(S)-α-Me-o-fluoroPhe-OH

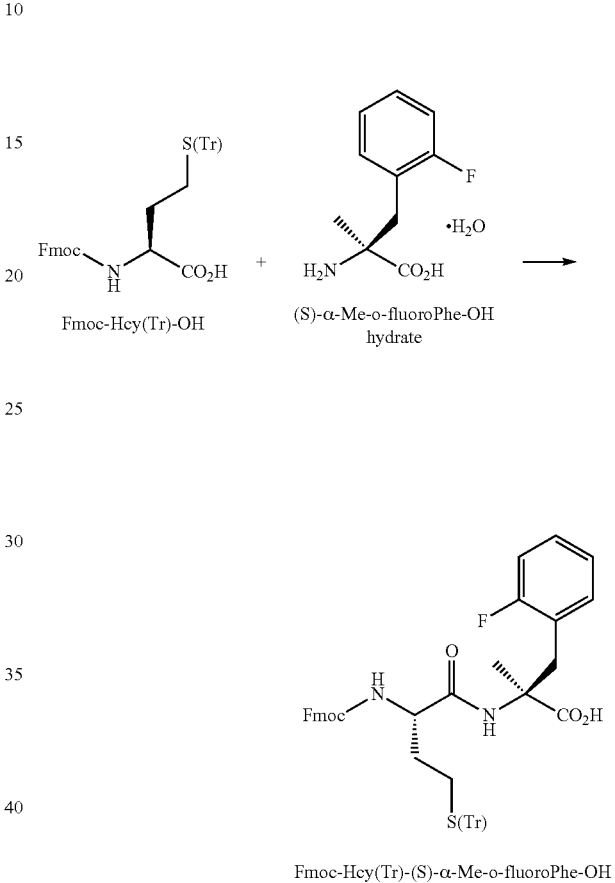

Fmoc-Hcy(Tr)-(S)-α-Me-o-fluoroPhe-OH

A 25 mL reaction vessel was charged with 0.23 g (0.42 mmol) of Fmoc-Hcy(Tr)-OH and 0.11 g (0.51 mmol) of (S)-α-Me-o-fluoroPhe-OH—H$_2$O, which were then suspended in THF (2 mL). To this suspension, 0.52 g (1.4 mmol) of HBTU and 0.20 mL (1.4 mmol) of TEA were added, and the mixture was stirred at room temperature for 3.2 hours. Tap water (2.5 mL) and ethyl acetate (4.3 mL) were added to the reaction mixture, and the mixture was stirred at room temperature and then left standing to separate between organic and aqueous layers. The organic layer was washed with a saturated aqueous solution of sodium bicarbonate (4 mL), 0.5 mol/L hydrochloric acid (2 mL), and tap water (6 mL) successively and then concentrated in vacuo. The residue was purified by silica gel column chromatography to give 0.11 g of Fmoc-Hcy(Tr)-(S)-α-Me-o-fluoroPhe-OH as a colorless oil (yield: 32%).

$^1$HNMR (400 MHz, CDCl$_3$) δ ppm: 1.48 (s, 3H); 1.5-1.7 (m, 1H); 1.7-1.9 (m, 1H); 2.1-2.4 (m, 2H); 3.28 (s, 2H); 4.0-4.1 (m, 1H); 4.1-4.2 (m, 1H); 4.2-4.3 (m, 1H); 4.3-4.4 (m, 1H); 5.25 (d, J=8.5 1H); 6.56 (br.s, 1H); 6.9-7.0 (m, 2H); 7.06 (t, J=6.8 Hz, 1H); 7.1-7.5 (m, 20H); 7.54 (d, J=7.0 Hz, 2H); 7.73 (d, J=7.0 Hz, 2H).

Example 6

Synthesis of Fmoc-D-Phe-(R)-α-(7-octenyl)Ala-OH

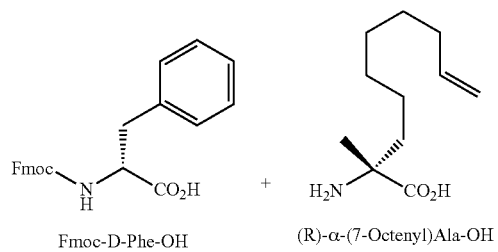

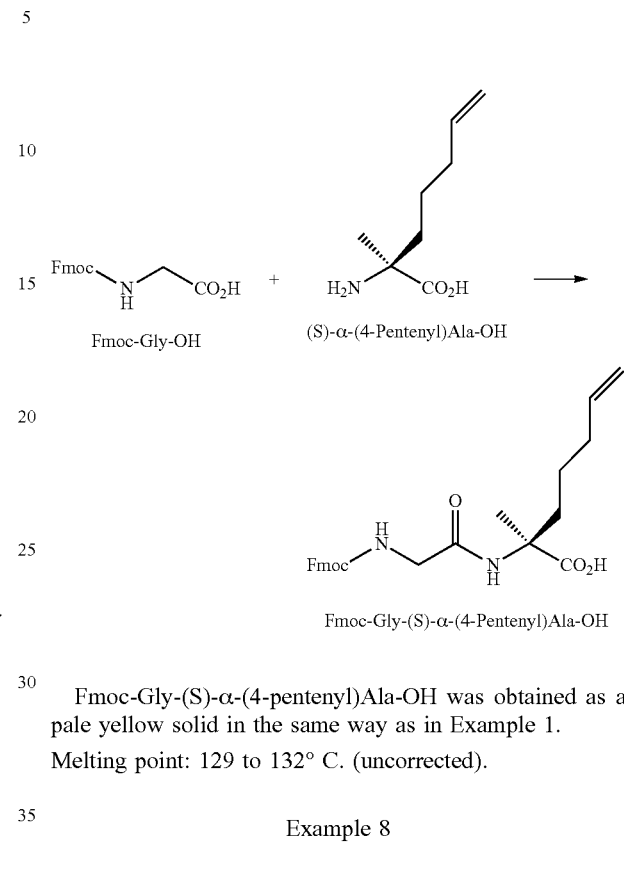

A 30 mL reaction vessel was charged with 0.69 g (1.8 mmol) of Fmoc-D-Phe-OH and 0.42 g (2.1 mmol) of (R)-α-(7-octenyl)Ala-OH, which were then suspended in THF (8.4 mL). To this suspension, 0.88 g (2.3 mmol) of HBTU and 0.37 mL (2.7 mmol) of TEA were added, and the mixture was stirred at room temperature for 31 hours.

Tap water (9 mL) and ethyl acetate (9 mL) were added to the reaction mixture, and the mixture was stirred at room temperature and then left standing to separate between organic and aqueous layers. To the organic layer, 0.5 mol/L hydrochloric acid (17 mL) was added, and the mixture was stirred at room temperature for 37 hours. Ethyl acetate (27 mL) was added thereto, and the mixture was washed with tap water (16 mL). Approximately 23 g of the solvent was concentrated. To the residue, tap water (8 mL) was added. After suction filtration, the precipitate was dried to give 0.47 g of Fmoc-D-Phe-(R)-α-(7-octenyl)Ala-OH as a white powder (yield: 46%).

$^1$HNMR (400 MHz, CDCl$_3$) δ ppm: 0.9-1.0 (m, 1H); 1.0-1.2 (m, 1H); 1.70 (t, J=13.3 Hz, 1H); 1.96 (dd, J$_1$=13.3 Hz, J$_2$=7.0 Hz, 2H); 2.09 (t, J=11.0 Hz, 1H); 2.9-3.1 (m, 1H); 3.0-3.2 (m, 1H); 4.18 (t, J=6.8 Hz, 1H); 4.2-4.4 (m, 2H); 4.56 (br.s, 1H); 4.8-5.0 (m, 2H); 5.63 (d, J=8.0 Hz, 1H); 5.6-5.8 (m, 1H); 6.54 (br.s, 1H); 7.2-7.3 (m, 5H); 7.30 (t, J=7.5 Hz, 2H); 7.39 (t, J=7.5 Hz, 2H); 7.54 (dd, J$_1$=7.5 Hz, J$_2$=2.2 Hz, 2H); 7.76 (d, J=7.5 Hz, 2H).

Example 7

Synthesis of Fmoc-Gly-(S)-α-(4-pentenyl)Ala-OH

Fmoc-Gly-(S)-α-(4-pentenyl)Ala-OH was obtained as a pale yellow solid in the same way as in Example 1.

Melting point: 129 to 132° C. (uncorrected).

Example 8

Synthesis of Fmoc-Arg (Pbf)-(S)-α-(4-pentenyl)Ala-OH

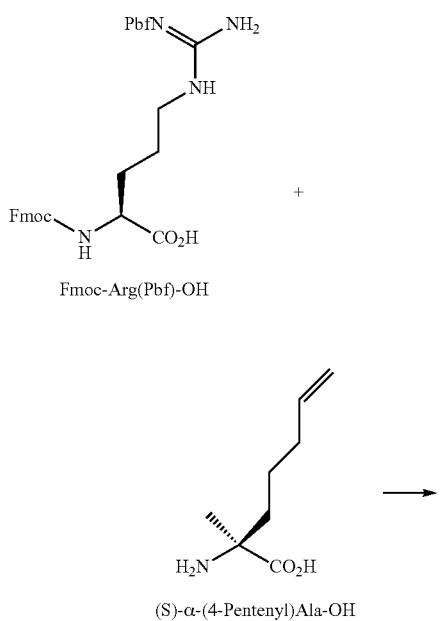

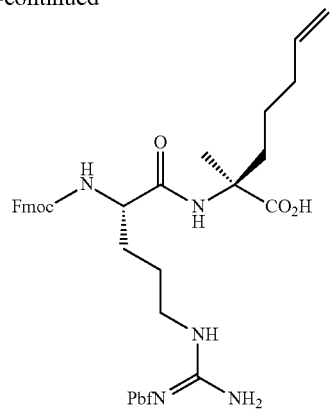

Fmoc-Arg(Pbf)-(S)-α-(4-Pentenyl)Ala-OH

Fmoc-Arg(Pbf)-(S)-α-(4-pentenyl)Ala-OH was obtained as a white amorphous solid in the same way as in Example 6.

Melting point: 102 to 147° C. (uncorrected).

¹HNMR (400 MHz, CDCl₃) δ ppm: 1.35 (br.s, 2H); 1.42 (s, 6H); 1.51 (s, 3H); 1.6-1.7 (m, 2H); 1.7-1.8 (m, 1H); 1.8-1.9 (m, 3H); 1.9-2.1 (m, 2H); 2.06 (s, 3H); 2.49 (s, 3H); 2.56 (s, 3H); 2.90 (s, 2H); 3.1-3.3 (m, 2H); 4.0-4.2 (m, 1H); 4.2-4.3 (m, 3H); 4.8-5.0 (m, 2H); 5.69 (dt, J₁=16.8 Hz, J₂=6.5 Hz, 1H); 6.42, 6.70 (br.s, 3H); 7.20 (t, J=7.6 Hz, 2H); 7.43 (t, J=7.6 Hz, 2H); 7.55 (d, J=7.6 Hz, 2H); 7.71 (d, J=7.6 Hz, 2H).

Example 9

Synthesis of Fmoc-Leu-(S)-α-(4-pentenyl)Ala-OH

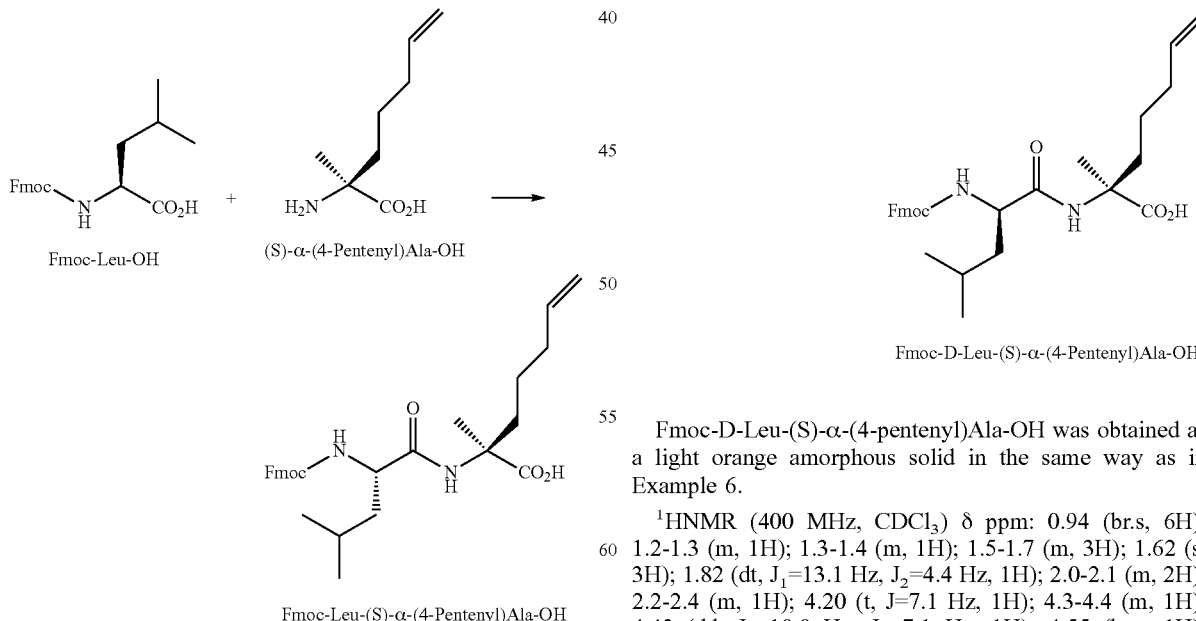

Fmoc-Leu-(S)-α-(4-pentenyl)Ala-OH

Fmoc-Leu-(S)-α-(4-pentenyl)Ala-OH was obtained as a light orange amorphous solid in the same way as in Example 6.

¹HNMR (400 MHz, CDCl₃) δ ppm: 0.8-1.0 (m, 6H); 1.1-1.3 (m, 1H); 1.2-1.4 (m, 1H); 1.5-1.7 (m, 3H); 1.62 (s, 3H); 1.84 (dt, J₁=12.8 Hz, J₂=4.0 Hz, 1H); 1.97 (dd, J₁=12.8 Hz, J₂=6.4 Hz, 2H); 2.30 (dt, J₁=12.8 Hz, J₂=4.0 Hz, 1H); 4.19 (t, J=7.0 Hz, 2H); 4.3-4.5 (m, 2H); 4.48 (br.s, 1H); 4.8-5.0 (m, 2H); 5.5-5.7 (m, 2H); 7.21 (br.s, 1H); 7.30 (dt, J₁=7.4 Hz, J₂=0.6 Hz, 2H); 7.39 (t, J=7.4 Hz, 2H); 7.57 (dd, J₁=7.4 Hz, J₂=2.8 Hz, 2H); 7.75 (d, J=7.5 Hz, 2H).

Example 10

Synthesis of Fmoc-D-Leu-(S)-α-(4-pentenyl)Ala-OH

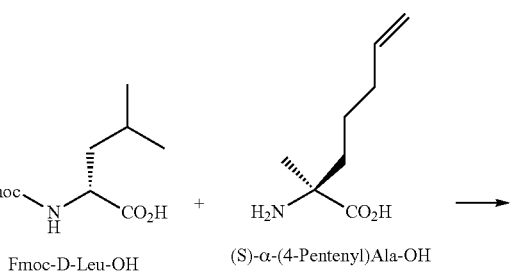

Fmoc-D-Leu-(S)-α-(4-Pentenyl)Ala-OH

Fmoc-D-Leu-(S)-α-(4-pentenyl)Ala-OH was obtained as a light orange amorphous solid in the same way as in Example 6.

¹HNMR (400 MHz, CDCl₃) δ ppm: 0.94 (br.s, 6H); 1.2-1.3 (m, 1H); 1.3-1.4 (m, 1H); 1.5-1.7 (m, 3H); 1.62 (s, 3H); 1.82 (dt, J₁=13.1 Hz, J₂=4.4 Hz, 1H); 2.0-2.1 (m, 2H); 2.2-2.4 (m, 1H); 4.20 (t, J=7.1 Hz, 1H); 4.3-4.4 (m, 1H); 4.42 (dd, J₁=10.0 Hz, J₂=7.1 Hz, 1H); 4.55 (br.s, 1H); 4.9-5.0 (m, 2H); 5.5-5.6 (m, 1H); 5.72 (dt, J₁=17.0 Hz, J₂=6.8 Hz, 1H); 7.21 (br.s, 1H); 7.30 (t, J=7.5 Hz, 2H); 7.39 (t, J=7.5 Hz, 2H); 7.57 (d, J=7.5 Hz, 2H); 7.76 (d, J=7.5 Hz, 2H).

Example 11

Synthesis of Fmoc-Phe-(R)-α-(7-octenyl)Ala-OH

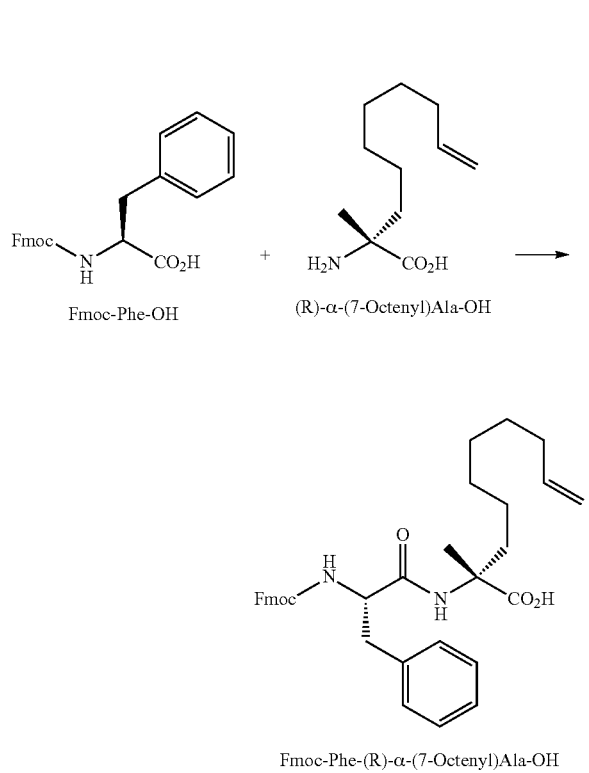

Fmoc-Phe-(R)-α-(7-octenyl)Ala-OH

Fmoc-Phe-(R)-α-(7-octenyl)Ala-OH was obtained as a white powder in the same way as in Example 6.

$^1$HNMR (400 MHz, CDCl$_3$) δ ppm: 1.0-1.1 (m, 2H); 1.21 (br.s, 4H); 1.32 (br.s, 2H); 1.53 (s, 3H); 1.6-1.8 (m, 1H); 1.9-2.0 (m, 2H); 2.0-2.1 (m, 1H); 3.0-3.1 (m, 2H); 4.15 (t, J=7.2 Hz, 1H); 4.2-4.3 (m, 1H); 4.35 (dd, J$_1$=10.2 Hz, J$_2$=7.2 Hz, 1H); 4.71 (br.s, 1H); 4.8-5.0 (m, 2H); 5.7-5.9 (m, 2H); 6.85 (br.s, 1H); 7.2-7.3 (m, 5H); 7.28 (t, J=7.5 Hz, 2H); 7.39 (t, J=7.5 Hz, 2H); 7.5-7.6 (m, 2H); 7.75 (d, J=7.5 Hz, 2H).

Production of N-Terminal Protected Dipeptide Using Monosubstituted Amino Acid

Comparative Example 1

Synthesis of Fmoc-Thr(Ot-Bu)-(S)-o-fluoroPhe-OH

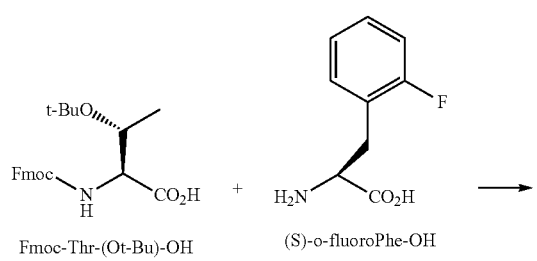

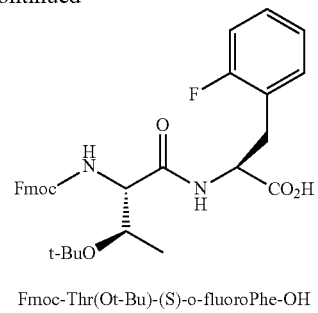

Fmoc-Thr(Ot-Bu)-(S)-o-fluoroPhe-OH

A 15 mL reaction vessel was charged with 97.06 mg (0.2442 mmol) of Fmoc-Thr(Ot-Bu)-OH and 56.61 mg (0.3090 mmol) of (S)-o-fluoroPhe-OH, which were then suspended in THF (1.2 mL). To this suspension, 0.28 g (0.74 mmol) of HBTU and 0.104 mL (0.746 mmol) of TEA were added, and the mixture was stirred at room temperature for 4.1 hours.

The reaction mixture was sampled in the course of the reaction and analyzed by HPLC (detection: 264 nm, UV). The area ratio of the respective peaks corresponding to Fmoc-Thr (Ot-Bu)-OH,
Fmoc-Thr (Ot-Bu)-o-fluoroPhe-OH (dipeptide),
Fmoc-Thr(Ot-Bu)-o-fluoroPhe-o-fluoroPhe-OH (tripeptide),
and
Fmoc-Thr(Ot-Bu)-o-fluoroPhe-o-fluoroPhe-o-fluoroPhe-OH (tetrapeptide)
was 72:11:12:5.7 (rate of reaction: 29%) in 1.8 hours, 72:9.9:13:5.3 (rate of reaction: 28%) in 3 hours, and 71:9.5:12:7.2 (rate of reaction: 29%) in 4.1 hours. The rate of reaction was calculated from the ratio of the area of Fmoc-Gly-OH to the total area of Fmoc-Thr(Ot-Bu)-OH, the dipeptide, the tripeptide, the tetrapeptide, and the pentapeptide (the peak of the pentapeptide was undetected).

The ratio between two main isomers of Fmoc-Thr(Ot-Bu)-o-fluoroPhe-OH was 54:46 in 1.8 hours, 53:47 in 3 hours, and 51:49 in 4.1 hours.
Fmoc-Thr(Ot-Bu)-o-fluoroPhe-OH;
HRMS m/z: 585.2371 (calcd for C$_{32}$H$_{35}$FN$_2$NaO$_6$ ([M+Na]$^+$)); 585.2371 (found).
Fmoc-Thr(Ot-Bu)-o-fluoroPhe-o-fluoroPhe-OH;
HRMS m/z: 728.3142 (calcd for C$_{41}$H$_{44}$F$_2$N$_3$O$_7$ ([M+H]$^+$)); 728.3138 (found).
Fmoc-Thr (Ot-Bu)-o-fluoroPhe-o-fluoroPhe-o-fluoroPhe-OH;
HRMS m/z: 893.3732 (calcd for C$_{50}$H$_{52}$F$_3$N$_4$O$_8$ ([M+H]$^+$)); 893.3729 (found).

As is evident from the results of Comparative Example 1, the production of a dipeptide using a monosubstituted amino acid without the protection of the carboxyl group of the amino acid formed a totally unpractical dipeptide because its carboxyl group was sequentially bound to amino acids resulting in oligomers. Furthermore, the formed dipeptide exhibited low stereoisomeric purity, and the mixtures containing almost equal amounts of the isomers were obtained. This is probably because the carboxy group can be activated even after the condensation reaction and therefore causes epimerization even if further condensation does not occur.

In contrast to this, as is evident from, for example, the results of Example 3, condensation reaction using a disubstituted amino acid was able to produce the desired compound at high yields without forming oligomers of concern, though the carboxyl group of the amino acid was not protected. Furthermore, use of the disubstituted amino acid did not cause epimerization in principle and also produced a compound having high stereoisomeric purity.

Production of Peptide

Reference Example 1

Synthesis of H-Leu-Arg-(S)-α-(4-pentenyl)Ala-Phe-NH$_2$

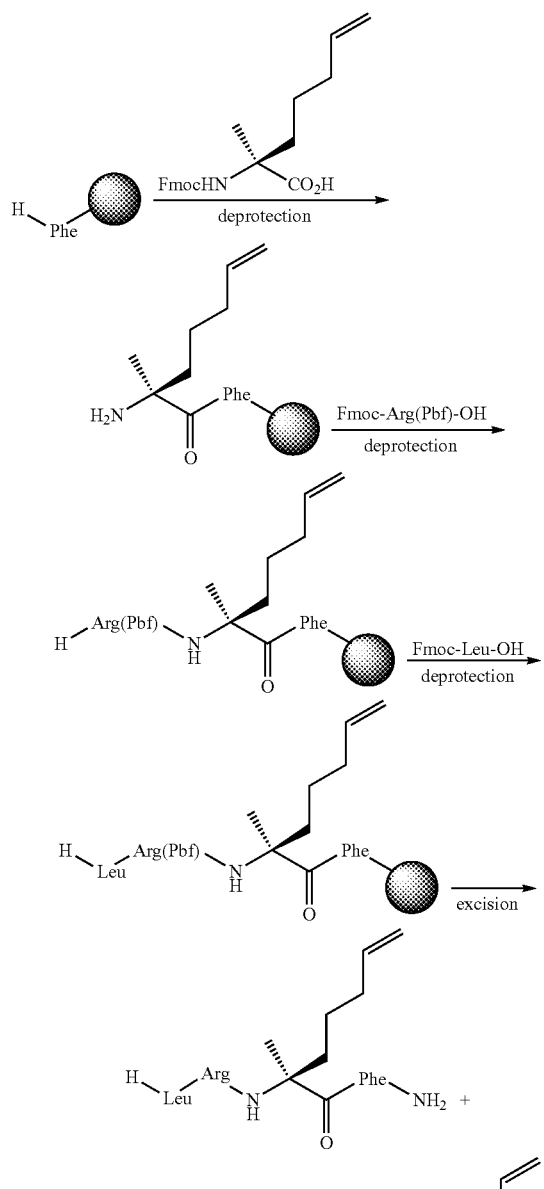

Four amino acid residues were bound by solid-phase peptide synthesis according to the Fmoc method using Rink Amide MBHA resin (100 to 200 mesh) as a support to synthesize H-Leu-Arg-(S)-α-(4-pentenyl)Ala-Phe-NH$_2$. The solvent used was NMP. The condensation conditions involved HBTU/HOBt/DIPEA. Fmoc was eliminated using piperidine. The peptide was dissociated from the support using TFA/tap water/triisopropylsilane. The product was contaminated with 25% (to the peptide of interest) H-Leu-(S)-α-(4-pentenyl)Ala-Phe-NH$_2$, in addition to the peptide of interest.

H-Leu-Arg-(S)-α-(4-pentenyl)Ala-Phe-NH$_2$;
HRMS m/z: 573.3871 (calcd for $C_{29}H_{49}N_8O_4$ ([M+H])); 573.3876 (found).
H-Leu-(S)-α-(4-pentenyl)Ala-Phe-NH$_2$;
HRMS m/z: 417.2860 (calcd for $C_{23}H_{37}N_4O_3$ ([M+H])); 417.2860 (found).

MS Data

Reference Example 2

Synthesis of H-Leu-Arg-(S)-α-(4-pentenyl)Ala-Phe-NH$_2$

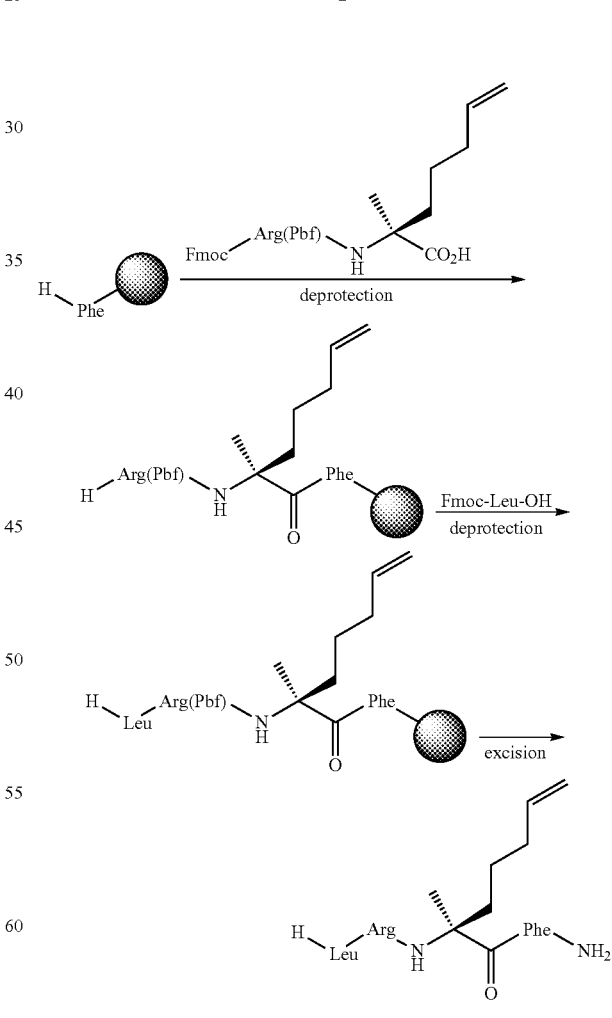

H-Leu-Arg-(S)-α-(4-pentenyl)Ala-Phe-NH$_2$ was synthesized in the same way as in Reference Example 1 using Fmoc-Arg(Pbf)-(S)-α-(4-pentenyl)Ala-OH prepared in Example 8 instead of Fmoc-Arg(Pbf)-OH and (S)-Fmoc-α-(4-pentenyl)Ala-OH. The peptide of interest was not contaminated with H-Leu-(S)-α-(4-pentenyl)Ala-Phe-NH₂.

HEMS m/z: 573.3871 (calcd for $C_{29}H_{49}N_8O_4$ ([M+H]⁺)); 573.3874 (found).

Reference Example 3

Synthesis of H-Leu-D-Hcy-(S)-α-Me-o-fluoroPhe-Phe-NH₂

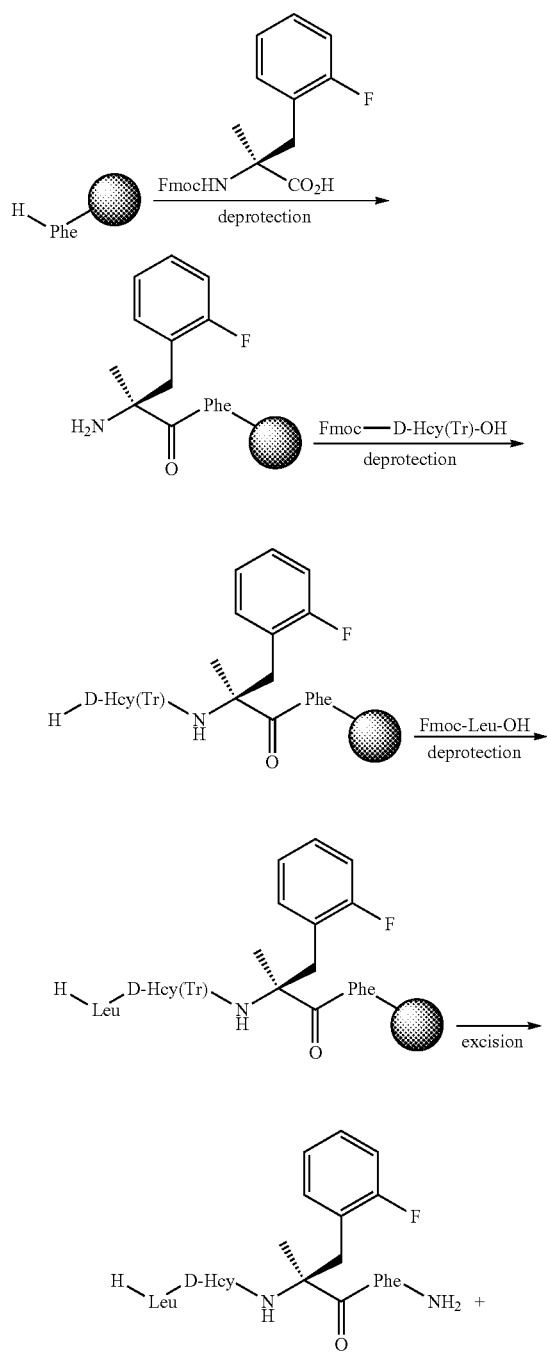

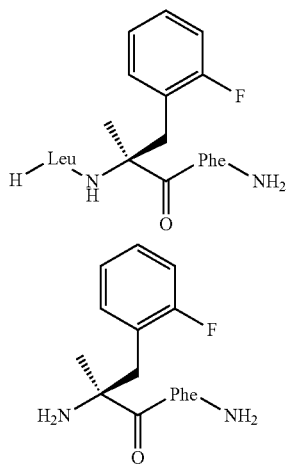

H-Leu-D-Hcy-(S)-α-Me-o-fluoroPhe-Phe-NH₂ was synthesized in the same way as in Reference Example 1. The product was contaminated with 1.0% (to the peptide of interest) H-Leu-(S)-α-Me-o-fluoroPhe-Phe-NH₂ and 1.2% (to the peptide of interest) H—(S)-α-Me-o-fluoroPhe-Phe-NH₂, in addition to the peptide of interest.

H-Leu-D-Hcy-(S)-α-Me-o-fluoroPhe-Phe-NH₂;

HRMS m/z: 574.2858 (calcd for $C_{29}H_{41}FN_5O_4S$ ([M+H]+)); 574.2856 (found).

H-Leu-(S)-α-Me-o-fluoroPhe-Phe-NH₂;

HRMS m/z: 457.2609 (calcd for $C_{25}H_{34}FN_4O_3$ ([M+H]⁺)); 457.2611 (found).

H—(S)-α-Me-o-fluoroPhe-Phe-NH₂;

HRMS m/z: 344.1769 (calcd for $C_{19}H_{23}FN_3O_2$ ([M+H]⁺)); 344.1761 (found).

Reference Example 4

Synthesis of H-Leu-D-Hcy-(S)-α-Me-o-fluoroPhe-Phe-NH₂

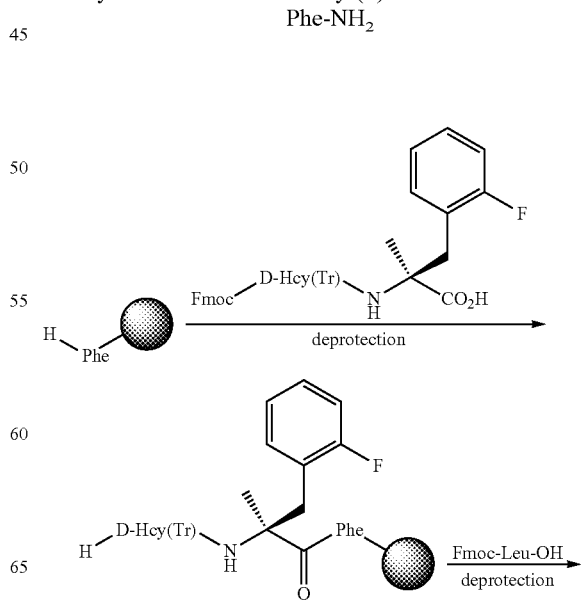

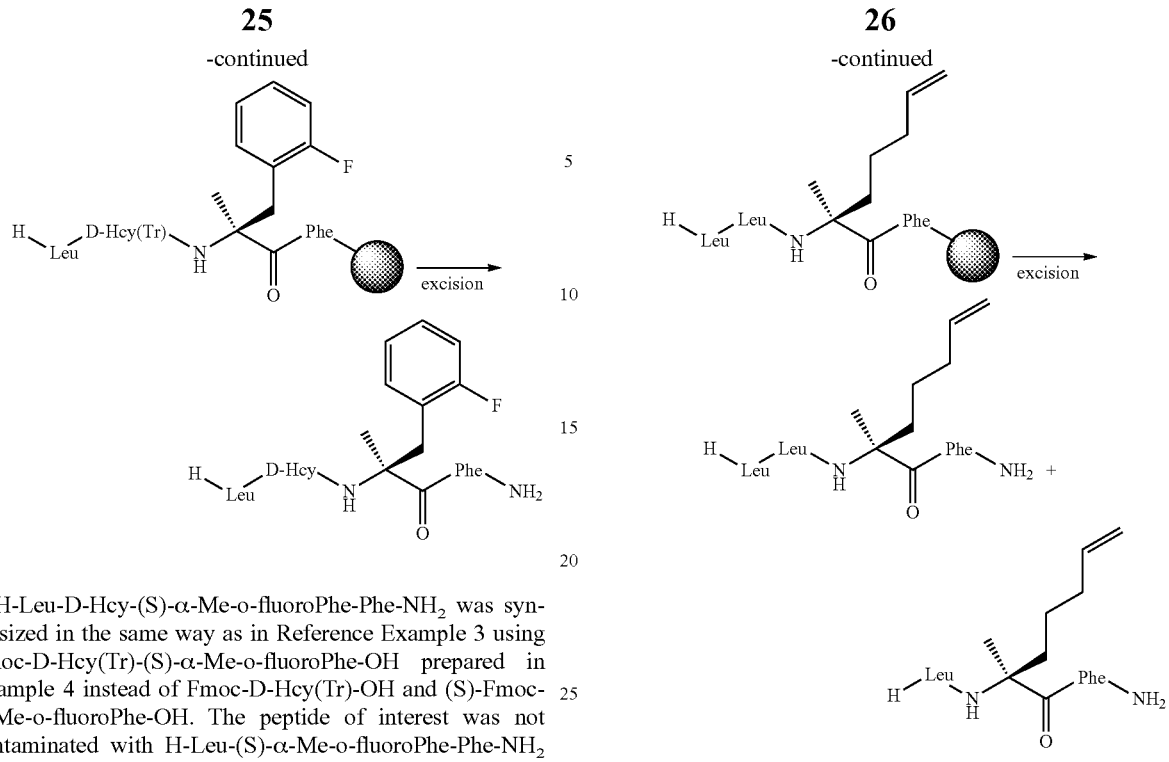

H-Leu-D-Hcy-(S)-α-Me-o-fluoroPhe-Phe-NH$_2$ was synthesized in the same way as in Reference Example 3 using Fmoc-D-Hcy(Tr)-(S)-α-Me-o-fluoroPhe-OH prepared in Example 4 instead of Fmoc-D-Hcy(Tr)-OH and (S)-Fmoc-α-Me-o-fluoroPhe-OH. The peptide of interest was not contaminated with H-Leu-(S)-α-Me-o-fluoroPhe-Phe-NH$_2$ and H—(S)-α-Me-o-fluoroPhe-Phe-NH$_2$.

HRMS m/z: 574.2858 (calcd for C$_{29}$H$_{41}$FN$_5$O$_4$S ([M+H]$^+$)); 574.2862 (found).

Reference Example 5

Synthesis of H-Leu-Leu-(S)-α-(4-pentenyl)Ala-Phe-NH$_2$

H-Leu-Leu-(S)-α-(4-pentenyl)Ala-Phe-NH$_2$ was synthesized in the same way as in Reference Example 1. The product was contaminated with 0.89% (to the peptide of interest) H-Leu-(S)-α-(4-pentenyl) Ala-Phe-NH$_2$, in addition to the peptide of interest.

H-Leu-Leu-(S)-α-(4-pentenyl)Ala-Phe-NH$_2$;
HRMS m/z: 530.3701 (calcd for C$_{29}$H$_{48}$N$_5$O$_4$ ([M+H])); 530.3702 (found).

H-Leu-(S)-α-(4-pentenyl)Ala-Phe-NH$_2$;
HRMS m/z: 417.2860 (calcd for C$_{23}$H$_{36}$N$_4$O$_3$ ([M+H]+)); 417.2856 (found).

Reference Example 6

Synthesis of H-Leu-Leu-(S)-α-(4-pentenyl)Ala-Phe-NH$_2$

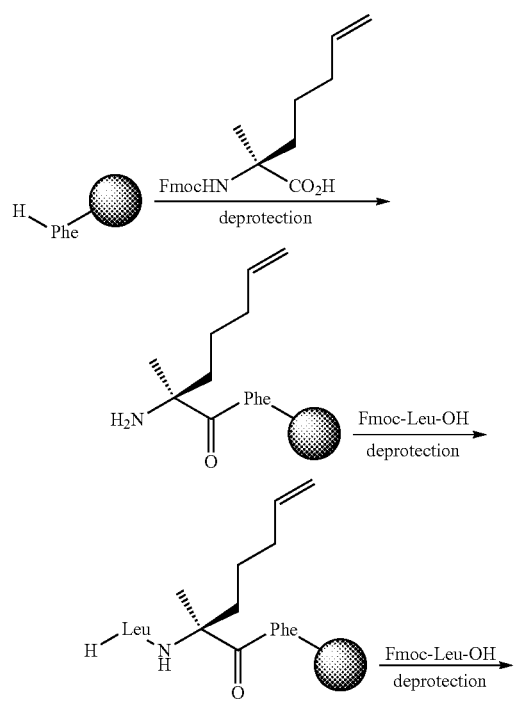

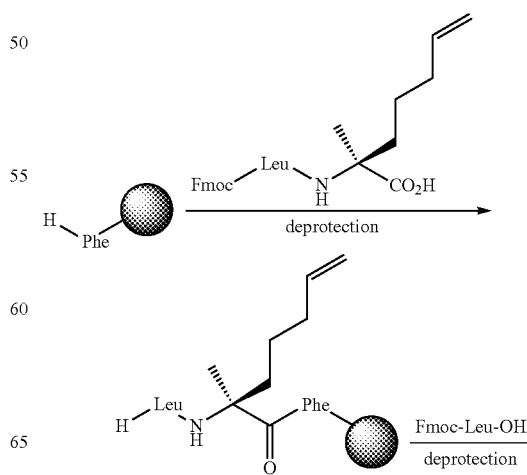

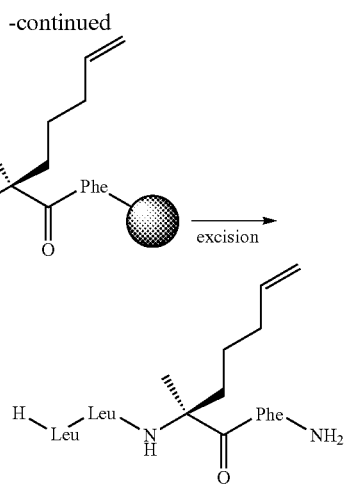

H-Leu-Leu-(S)-α-(4-pentenyl) Ala-Phe-NH$_2$ was synthesized in the same way as in Reference Example 5 using Fmoc-Leu-(S)-α-(4-pentenyl)Ala-OH prepared in Example 9 instead of Fmoc-Leu-OH and (S)-Fmoc-α-(4-pentenyl) Ala-OH. The peptide of interest was not contaminated with H-Leu-(S)-α-(4-pentenyl)Ala-Phe-NH$_2$.

HRMS m/z: 530.3701 (calcd for C$_{29}$H$_{48}$N$_5$O$_4$ ([M+H]+)); 530.3708 (found).

In Reference Examples 1, 3, and 5 in which amino acids were sequentially bound according to the conventional solid-phase peptide synthesis method, the desired peptide was confirmed to be contaminated with amino acid-defective forms. By contrast, in Reference Examples 2, 4, and 6 using the dipeptide derivatives produced by the production method according to the present invention to synthesize similar peptides, the contamination of such amino acid-defective forms was not observed.

INDUSTRIAL APPLICABILITY

The present invention can provide a method for producing a dipeptide derivative, which requires a fewer number of steps than that of the conventional method for producing a dipeptide and is capable of producing the desired dipeptide derivative at high yields, regardless of the type of a protecting group in the side chain of each constituent amino acid.

The invention claimed is:

1. A method for producing an N-terminal protected dipeptide represented by the following formula (1) or a salt thereof:

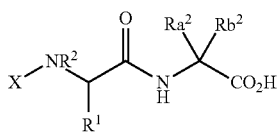

Formula (1)

wherein X represents a protecting group for an amino group,
R$^1$ represents a side chain of an α-monosubstituted amino acid, or a hydrogen atom, wherein the side chain is optionally protected,
R$^2$ represents a group bonded to R$^1$ to form the side chain, or a hydrogen atom, and
R$^{a2}$ and R$^{b2}$ each independently represent an alkyl group optionally having a substituent, an alkenyl group optionally having a substituent, an alkynyl group optionally having a substituent, or an aralkyl group optionally having a substituent,
the production method comprising condensing
an N-terminal protected α-monosubstituted amino acid or glycine represented by the following formula (2), or a salt of the amino acid or glycine:

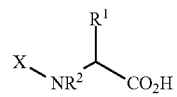

Formula (2)

wherein X, R$^1$, and R$^2$ are as defined for X, R$^1$, and R$^2$, respectively, in the formula (1),
with a disubstituted amino acid represented by the following formula (3) or a salt thereof:

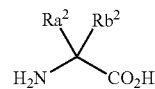

Formula (3)

wherein R$^{a2}$ and R$^{b2}$ are as defined for R$^{a2}$ and R$^{b2}$, respectively, in the formula (1) in the presence of a condensing agent.

2. The production method according to claim 1, wherein the N-terminal protected α-monosubstituted amino acid or glycine represented by the formula (2), or a salt of the amino acid or glycine is condensed with the disubstituted amino acid represented by the formula (3) or a salt thereof in the presence of a stoichiometric amount or more of the condensing agent.

3. The production method according to claim 1, wherein the reaction of the N-terminal protected α-monosubstituted amino acid or glycine represented by the formula (2), or a salt of the amino acid or glycine with the disubstituted amino acid represented by the formula (3) or a salt thereof is terminated when the rate of reaction of the N-terminal protected α-monosubstituted amino acid or glycine represented by the formula (2), or a salt of the amino acid or glycine reaches 70 to 80%.

4. The production method according to claim 2, wherein the reaction of the N-terminal protected α-monosubstituted amino acid or glycine represented by the formula (2), or a salt of the amino acid or glycine with the disubstituted amino acid represented by the formula (3) or a salt thereof is terminated when the rate of reaction of the N-terminal protected α-monosubstituted amino acid or glycine represented by the formula (2), or a salt of the amino acid or glycine reaches 70 to 80%.

* * * * *

UNITED STATES PATENT AND TRADEMARK OFFICE
CERTIFICATE OF CORRECTION

PATENT NO.       : 9,605,020 B2  
APPLICATION NO.  : 14/914458  
DATED            : March 28, 2017  
INVENTOR(S)      : K. Matsuyama et al.

Page 1 of 1

It is certified that error appears in the above-identified patent and that said Letters Patent is hereby corrected as shown below:

In the Claims

Column 28, Line 7 Claim 1, change "$R^{a2}$ and $R^{b2}$" to -- $Ra^2$ and $Rb^2$ --.

Column 28, Line 34 Claim 1, change "$R^{a2}$ and $R^{b2}$ are as defined for $R^{a2}$ and $R^{b2}$," to -- $Ra^2$ and $Rb^2$ are as defined for $Ra^2$ and $Rb^2$, --.

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*